(12) United States Patent
Perrier et al.

(10) Patent No.: US 6,235,294 B1
(45) Date of Patent: May 22, 2001

(54) FLAVONOIDE ESTERS AND THEIR USE NOTABLY IN COSMETICS

(75) Inventors: Eric Perrier, Les Cotes D'Arey; Anne-Marie Mariotte, St. Simeon De Bressieux; Ahcéne Boumendjel, La Tronche; Delphine Bresson-Rival, Lyons, all of (FR)

(73) Assignee: Coletica, Lyons (FR)

( * ) Notice: Subject to any disclaimer, the term of this patent is extended or adjusted under 35 U.S.C. 154(b) by 0 days.

(21) Appl. No.: 09/113,158

(22) Filed: Jul. 10, 1998

(30) Foreign Application Priority Data

May 15, 1998 (FR) .................................................. 98 06194

(51) Int. Cl.$^7$ ...................................................... A61K 6/00
(52) U.S. Cl. ........................... 424/401; 424/59; 514/456; 514/844; 514/886; 514/887; 514/969; 549/283; 549/285
(58) Field of Search ...................... 424/401, 59; 514/844, 514/886, 887, 969, 456; 549/283, 285

(56) References Cited

U.S. PATENT DOCUMENTS 5,882,658 * 3/1999 Simon et al. ........................ 424/401

FOREIGN PATENT DOCUMENTS

| | | |
|---|---|---|
| 0019 081 A1 | 9/1980 | (EP) . |
| 0206 219 A1 | 12/1986 | (EP) . |
| 0709 383 A1 | 5/1996 | (EP) . |
| 55-157580 | 12/1980 | (JP) . |
| 60-100570 | 6/1985 | (JP) . |
| 09118611 * | 5/1997 | (JP) . |
| 5813911 * | 3/1998 | (JP) . |
| WO 94/29404 | 12/1994 | (WO) . |
| WO 95/21018 | 8/1995 | (WO) . |
| 9811889 * | 3/1998 | (WO) . |
| WO 98/11889 | 3/1998 | (WO) . |

OTHER PUBLICATIONS

Database WPI Section Ch, Week 8528 Derwent Publications Ltd., London, GB; Class B02, AN 85–169461—XP002090945—& JP 60 100570 A (Otsuka Pharm Co Ltd) (Abstract) Jun. 4, 1985.

Database WPI, Section Ch, Week 8107; Derwent Publications Ltd., London, GB; Class D21; AN 81–10549D; XP002090946—& JP 55 157580 A (Sansho Seiyaku KK) (Abstract). Dec. 8, 1980.

Chemical Abstracts, vol. 69, No. 25, Dec. 16, 1968; Columbus, Ohio, US; Abstract No. 107018; Yamabe, Shigeru et al: "Ester of fatty acid with rutin"—XP002090941 & JP 43 011894 A (Sumitomo Chemical Co., Ltd) (Abstract).

Chemical Abstracts, vol. 117, No. 7; Aug. 17, 1992; Columbus, Ohio, US; Abstract No. 66563; Maldonado, Emma et al; "Acylated flavonols and other constituents from Galeana pratensis"—XP002090942 & Phytochemistry (1992), 31(3), 1003–7; ISSN:0031–9422 (Abstract).

Chemical Abstracts, vol. 113, No. 9, Aug. 27, 1990; Columbus, Ohio; US; Abstract No. 74850; Urzua, Alejandro et al: "Acylated flavonoid aglycons from Gnaphalium robustum"—XP002090943 & Phytochemistry (1990), 29(4), 1342–3 (Abstract).

Chemical Abstracts, vol. 113, No. 3, Jul. 16, 1990, Columbus, Ohio, US; Abstract No. 24355; Danieli, Bruno et al: "Enzyme–mediated acylation of flavonoid monoglycosides"—XP002090944 & Heterocycles (1989), 29(11), 2061–4; ISSN: 0385–5414 (Abstract).

Danieli, Bruno et al.: "Enzyme–mediated Regioselective Acylations of Flavonoid Disaccharide monoglycosides," HELV. Chim. Acta (1990), 73(7), 1837–44 Coden: HCACAV; ISSN: 0018–019X—XP002090940.

* cited by examiner

*Primary Examiner*—Thurman K. Page
*Assistant Examiner*—Lakshmi Channavajjaia
(74) *Attorney, Agent, or Firm*—Armstrong, Westerman, Hattori, McLeland & Naughton, LLP

(57) ABSTRACT

The invention relates to a flavonoid ester. This flavonoid ester results from the reaction product of at least one flavonoid selected from the group consisting of a flavonoid with a ketone group in the 4-position, a salt, ester or ether of such a flavonoid, and a C-heteroside and/or O-heteroside derivative of such a flavonoid, with the proviso that this flavonoid contains at least one free alcohol group, with an organic monoacid having from 3 to 30 carbon atoms. These flavonoid esters constitute useful active principles for the manufacture of cosmetic, dermopharmaceutical, pharmaceutical, dietetic or agri-foodstuff compositions.

12 Claims, No Drawings

FLAVONOIDE ESTERS AND THEIR USE NOTABLY IN COSMETICS

The invention relates essentially to novel flavonoid esters, to their use in cosmetics, dermopharmacy, pharmacy, dietetics and agri-foodstuffs, and to cosmetic, dermopharmaceutical, pharmaceutical, dietetic and agri-foodstuff compositions in which said flavonoid esters are used.

Within the framework of the invention, it has been discovered, surprisingly and unexpectedly, that specific flavonoid esters can be stabilized while at the same time preserving their initial property, particularly of free radical inhibition and enzyme inhibition, and for applications associated with these properties:

venous tonics, agents for increasing the strength of the blood capillaries, inhibitors of blotchiness, inhibitors of chemical, physical or actinic erythema, agents for treating sensitive skin, decongestants, draining agents, slimming agents, anti-wrinkle agents, stimulators of the synthesis of the components of the extracellular matrix, toners for making the skin more elastic, and anti-ageing agents.

STATE OF THE ART

Flavonoids are pigments found almost universally in plants. They are responsible for the coloration of the flowers, the fruits and sometimes the leaves. This is the case of the yellow flavonoids (chalcones, aurones, certain flavonols) and red, blue or violet anthocyanosides. They can also contribute to coloration via their role as copigments: thus colorless flavones and flavonols copigment and protect anthocyanosides.

Flavonoids absorb in the UV and their universal presence in the foliar cuticle and the epidermal cells of leaves enables them to protect the plant tissues against the harmful effects of UV radiation.

The approximately 3000 flavonoids known have a common biosynthetic origin and hence possess the same basic structural element, namely the 2-phenyl-chroman linkage. They can be grouped in different classes according to the degree of oxidation of the central pyran ring: thus a distinction is drawn between anthocyans, 2-phenylchromones (flavones, flavonols and their dimers, flavanones and dihydroflavonols), 3-phenylchromans (isoflavones and isoflavanones, etc.), 2-phenylchromans (flavans, flavan-3-ols, flavan-3,4-diols), chalcones, dihydrochalcones and aurones.

These flavonoids can be glycosylated, in which case they are called heterosides. The osidic moiety can be mono-, di- or tri-saccharidic. The monoosides are formed with D-glucose, but also with D-galactose or D-allose, with pentoses (D-apiose, L-arabinose, L-rhamnose, D-xylose) or with D-glucuronic and D-galacturonic acids. The structural variability increases for the heterosides whose osidic moiety is a disaccharide or trisaccharide, which can be linear or branched.

Two types of heterosides have been described, namely O-glycosides and C-glycosides. In the case of the O-glycosides, the bond between the genin and the ose can be formed via any one of the phenolic hydroxyls of the genin, but as a general rule it is particularly the hydroxyl in the 7-position of flavones and the hydroxyl in the 3-position of flavonols which are involved. In the case of the C-glycosides, the bond is formed between the anomeric carbon of the sugar and the carbon in the 6-position or 8-position of the genin.

The Known Biological Properties of Flavonoids

Being potentially active on the veins, flavonoids reduce the permeability of the blood capillaries and increase their strength. This "vitamin P" property is historically associated with the observation that certain manifestations of scurvy which are cured by the administration of lemon juice are not cured by the administration of vitamin C alone. It was therefore postulated that ascorbic acid could only act in association with a factor "P", identified with flavonoids. Often anti-inflammatories (apigenol, chrysin, taxifolin, 8-glycosylhypolaetin, gossypin, etc.), flavonoids can be antiallergics, liver protectors (isobutrin, hispidulin, flavanolignans, etc.), antispasmodics (flavonoids from thyme, etc.), hypocholesterolemics, diuretics, antibacterials, antivirals and cytostatics.

They are active in the regeneration of ascorbic acid in vivo via glutathione. More generally, flavonoids are scavengers of free radicals formed under various circumstances:

anoxia, which blocks the electron flow upstream of the cytochrome oxidases and causes the production of the superoxide radical anion;

inflammation, which corresponds inter alia to the production of superoxide anions by the membrane NADPH oxidase of the leukocytes, but also to the production (by disproportionation in the presence of ferrous ions) of the hydroxyl radical and other reactive species normally involved in the phenomenon of phagocytosis;

lipidic auto-oxidation, which is generally initiated by a hydroxyl radical and produces lipophilic alkoxy radicals via hydroperoxides.

Numerous flavonoids react with free radicals, thereby preventing the degradations associated with their intense reactivity towards the membrane phospholipids.

Flavonoids: Enzyme Inhibitors

As a general rule, flavonoids are enzyme inhibitors in vitro:

inhibition of histidine decarboxylase;

inhibition of protein kinases;

inhibition of elastase;

inhibition of hyaluronidase, which would make it possible to preserve the integrity of the ground substance of the vascular sheaths;

non-specific inhibition of catechol O-methyltransferase, which would increase the amount of catecholamines available and would therefore cause an increase in the vascular strength;

inhibition of cAMP phosphodiesterase, which could explain, inter alia, their platelet aggregation inhibiting activity;

inhibition of aldose reductase;

several flavonoids, monomeric flavonols and biflavonoids are potent inhibitors of lipoxygenase and/or cyclooxygenase, which, for many authors—at least as far as the inhibition of cyclooxygenase is concerned—is directly related to their capacity to scavenge free radicals. These properties, demonstrated in vitro, could explain, in the majority of cases, the anti-inflammatory and antiallergic activities recognized by numerous authors in several drugs known to contain flavonoids.

However, a number of major problems do not allow flavonoids to be used in a large number of cosmetic, pharmaceutical, dietetic or agri-foodstuffs applications:

It is extremely difficult to dissolve flavonoids and heterosides; thus, for example, heterosides are preferentially water-soluble, but this solubility is very low (rutoside, hesperidoside, etc.). Genins are preferentially soluble in apolar organic solvents, but here again this solubility is generally very low. These solubility problems can sometimes be solved by using extremely sophisticated excipients, although these are not suitable for the widespread use of flavonoids.

These flavonoids may or may not be colored, but in all cases their antioxidizing character and their very high reactivity towards oxygen or light makes them particularly unstable, and preparations, solutions, gels or emulsions containing them undergo spectacular color changes with time (white emulsions which become brown with time).

The concentration of these molecules in plant extracts is generally low and the stated activities are not systematically found in plant extracts.

Various solutions have been proposed in attempts to stabilize flavonoids.

For example, the document WO95/21018 to CNRS describes the preparation of microcapsules having walls crosslinked with plant polyphenols in order to stabilize the polyphenols, the polyphenols stabilized by crosslinking preserving their initial activity.

Also, the document WO94/29404 describes compositions of polyphenol derivatives, consisting of flavan derivatives and especially flavan-3-ol, for the stabilization of said compositions. In practice, said document essentially proposes the use of flavanolic oligomers or procyanolidic oligomers, abbreviated to PCO, in the form of stabilized derivatives.

All these flavans or flavanols are unsubstituted in the 4-position of the flavonoid heterocycle.

OBJECTS OF THE INVENTION

As already described in the above-cited documents of the prior art, i.e. WO95/21018 and WO94/29404, flavonoids are phenolic compounds with valuable antioxidizing properties. The use of these compounds is hampered by the problem of their instability due to the presence of these free phenolic groups, which oxidize readily on contact with oxygen or light to give free radical condensation compounds responsible for the appearance of coloration, making them inappropriate for use in a cosmetic application.

The main object of the present invention is to solve the new technical problem consisting in the provision of a solution which makes it possible to use a particular group of flavonoids, namely those with a ketone group in the 4-position, also called phenylchromones or 3-pyrones, in a sufficiently stable form to be usable particularly in the fields of cosmetics, dermopharmaceutics, pharmaceutics, dietetics and agri-foodstuffs, while at the same time preserving the initial properties of these flavonoids.

A further object of the invention is to provide a solution which makes it possible to use flavonoids with a ketone group in the 4-position, as well as their salts, esters or ethers, or osidic derivatives containing at least one or several C-heteroside and/or O-heteroside linkages, in forms stabilized for use especially in cosmetic, dermopharmaceutical, pharmaceutical, dietetic or agri-foodstuff compositions, without losing the initial properties of these compounds.

A further object of the invention is not only to stabilize said flavonoids, as well as their derivatives mentioned above, but also to provide a lipophilic form which gives these compounds liposoluble properties and also gives them especially a greater affinity for the cell membrane and specifically the cutaneous layers.

All these objects are achieved for the first time by the present invention in a simple, reliable and reproducible manner which can be used on the industrial, cosmetic, pharmaceutical, dietetic or agri-foodstuffs scale.

Thus, according to a first aspect, the present invention provides flavonoid esters which result from the reaction product of at least one flavonoid selected from the group consisting of a flavonoid with a ketone group in the 4-position, a salt, ester or ether of such a flavonoid, and such a flavonoid containing at least one or several C-heteroside and/or O-heteroside linkages, with the proviso that this flavonoid contains at least one free alcohol group, with an organic monoacid having from 3 to 30 carbon atoms. This monoacid can have a saturated or unsaturated, linear, branched or cyclic chain.

The above-mentioned organic monoacid can of course be selected from all organic monoacids with a saturated or unsaturated, linear or branched alkyl radical having from 3 to 30 carbon atoms, preferably from 4 to 22 carbon atoms.

In one advantageous embodiment of the invention, the above mentioned organic monoacid is selected from the group consisting of butyric acid (C4:0), valeric acid (C5:0), hexanoic acid (C6:0), sorbic acid (C6:2), ascorbic acid, lauric acid (C12:0), palmitic acid (C16:0), stearic acid (C18:0), oleic acid (C18:1), linoleic acid (C18:2), linolenic acid (C18:3), undecylenic acid (C11:1), heptanoic acid (C7), arachidonic acid (C20:4), eicosapentanoic acid (C20:5) and docosahexanoic acid (C22:6 and C24:1).

In yet another advantageous embodiment of the invention, the above-mentioned flavonoid with a ketone group in the 4-position has the following structural chemical formula (I) or (II):

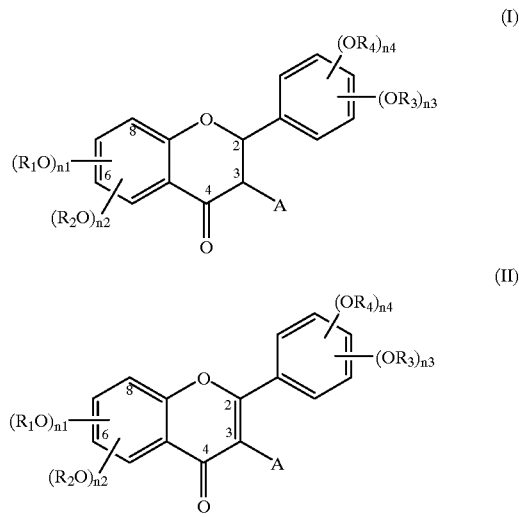

in which:
the groups $(OR_1)$ to $(OR_4)$ are in any position on the ring;
A is a hydrogen atom, a substituent R, a group —OH or a group —OR, R being as defined for the radicals $R_1$ to $R_4$;
$n_1$ and $n_2$, which are identical to or different from one another, are integers from 0 to 4, it being possible for the total of $n_1+n_2$ to be equal to at most 4, corresponding to the maximum number of substitutions on the ring;
$n_3$ and $n_4$, which are identical to or different from one another, are integers from 0 to 5, the total of $n_3+n_4$ being equal to a maximum of 5, representing the maximum number of substitutions on the ring; and $R_1$, $R_2$, $R_3$ and $R_4$ are each independently a hydrogen atom, an alkyl group having from 1 to 30 carbon atoms, particularly a saturated or unsaturated, linear, branched or cyclic lower alkyl group having from 1 to 6 carbon atoms, an acyl group with a saturated or unsaturated, linear, branched or cyclic alkyl radical having from 1 to 30 carbon atoms, preferably from 1 to 8 carbon atoms, or a simple or complex ose which may or may not contain alkyl or acyl groups with saturated or unsaturated, linear, branched or cyclic hydrocarbon chains having from 1 to 30 carbon atoms, with the proviso that at least one of the substituents R is a hydrogen atom, thereby defining at least one free hydroxyl group;

and the isomers of these units.

In yet another advantageous embodiment of the invention, the above mentioned starting flavonoid is a non-glycosylated flavone, particularly of formula (II) given above, for example apigenol (or apigenin) or luteolol, or a glycosylated flavone, for example diosmin, orientin, saponarin or shaftoside.

In yet another advantageous embodiment of the invention, the starting flavonoid is a non-glycosylated flavonol, particularly of formula (II) given above, for example kaempferol or quercetol (or quercetin), or a glycosylated flavonol, for example rutin, quercitroside, hyperoside, isoquercitroside or tiliroside.

In yet another advantageous embodiment of the invention, the starting flavonoid is a non-glycosylated or glycosylated dihydroflavonol, particularly of formula (II) given above, for example dihydrokaempferol or dihydroquercetol.

In yet another advantageous embodiment of the invention, the starting flavonoid is a non-glycosylated flavanone, particularly of formula (I) given above, for example naringetol (or naringenin), eriodictyol, hesperitin, eucalyptin, cirsimaritin, cajaflavanone, hinokiklavone, amentaflavone or bilobetol, or a glycosylated flavanone, for example hesperidin or naringin.

In yet another advantageous embodiment of the invention, the ose or oside substituting the above-mentioned flavonoid is selected from rhamnose, galactose, glucose and arabinose, which may or may not be substituted, the heteroside preferably being selected from tiliroside, orientin, shaftoside, saponarin, rutin, hesperidin and diosmin.

The flavonoid esters according to the invention could be prepared despite the much lower reactivity of the derivatives which have a ketone group in the 4-position, compared with those described in the prior art which do not have this ketone group; furthermore, the products of the invention have a particularly high stability while at the same time retaining their initial property, an observation which is totally unexpected and not obvious to those skilled in the art.

Moreover, the compounds of the invention have a lipophilic activity, giving them a liposoluble character and, specifically, an affinity for the cell membranes and particularly the tissues of the epidermis, which again is totally surprising.

According to a second aspect, the present invention also covers the use of the flavonoid esters according to the invention as cosmetic agents and as active principles for the manufacture of cosmetic, dermopharmaceutical, pharmaceutical, dietetic or agri-foodstuff compositions.

According to a third aspect, the present invention also covers a composition, selected especially from the group consisting of a cosmetic composition, a dermopharmaceutical composition, a pharmaceutical composition, a dietetic composition and an agri-foodstuff composition, which comprises, as one of its active agents, at least one flavonoid ester as defined above. These compositions are advantageously free radical inhibiting and enzyme inhibiting compositions; furthermore, especially in the context of a cosmetic, pharmaceutical or agri-foodstuffs application, these compositions can be used, depending on the particular case and the particular person, for carrying out a tonic treatment for the veins, a treatment for increasing the strength of the blood capillaries, an inhibiting effect on blotchiness, an inhibiting effect on chemical, physical or actinic erythema, a treatment for sensitive skin, a decongesting effect, a draining effect, a slimming effect, an anti-wrinkle effect, a stimulating effect on the synthesis of the components of the extracellular matrix of the epidermis, a toning effect on the epidermis, an improving effect on the elasticity of the skin and an anti-ageing effect on the skin.

The compositions according to the invention can be applied topically, it being advantageous also to use an appropriate vehicle, excipient or carrier, particularly one which is cosmetically, dermopharmaceutically or pharmaceutically acceptable, or a vehicle, excipient or carrier appropriate for use in dietetics or agri-foodstuffs.

Such vehicles, excipients or carriers are well known to those skilled in the art and are also apparent from the Formulation Examples discussed below. Reference may also be made to the excipients mentioned in the document WO95/21018, Examples 38–40, or the document WO94/29404, Examples 19–23, which are incorporated here by way of reference.

Within the framework of the invention, as all the initial biological properties of the flavonoids are preserved, all the biological properties stated above are claimed as forming part of the present invention in the context of the flavonoid esters of the invention.

The invention also covers a process for the synthesis of the above mentioned flavonoid esters, which comprises the acylation of at least one flavonoid selected from the group consisting of a flavonoid with a ketone group in the 4-position, a salt, ester or ether of such a flavonoid, and such a flavonoid containing at least one or several C-heteroside and/or O-heteroside linkages, with an organic monoacid having from 3 to 30 carbon atoms.

The conditions under which such acylations are carried out are well known to those skilled in the art; they can be carried out chemically (solvents) or enzymatically (lipase(s) in an anhydrous medium).

In another embodiment of the invention, this acylation can be carried out on one or more or even all of the alcohol groups of the flavonoid. This acylation can be carried out by various chemical methods of synthesis well known to those skilled in the art.

A first method consists in performing a chemical reaction which enables at least one free —OH group to be replaced with an acyl radical of the type —OCOR.

The acylating agent can advantageously be selected from acids of the formula RCOOH and the derivatives of such acids, particularly the acid halides of the formula RCOHal, the anhydrides of the formula RCOOCR or the esters of the formula RCOOR', R being for example a $C_1$–$C_{30}$ alkyl radical and R' preferably being a $C_1$–$C_6$ alkyl radical.

If an acid is used as the acylating agent, the reaction can be carried out in the presence of an activating agent for said acid, said activating agent normally being selectable from dicyclohexylcarbodiimide and tert-butyl chloroformate, which makes it possible to form a mixed anhydride.

The acylation reaction can be carried out in conventional manner in the presence of a solvent to allow partial solubilization of the starting polyphenolic compounds.

Appropriate solvents are selected for example from aromatic solvents such as toluene, an amine such as pyridine, a halogenated derivative such as chloroform and an oxygenated solvent such as acetone.

The reaction is preferably carried out at a temperature equal to at least 60° C. or, preferably, at the reflux temperature of the solvent, for a sufficient period of time to effect the acylation.

Within the framework of the invention, the acylation reaction is much more difficult to carry out than in the case of flavonoids which do not have ketone substitution in the 4-position of the heterocycle, so those skilled in the art did not expect to be able to prepare such esters, that they would be stable and that they would preserve the initial activity of the flavonoids, without degradation of these flavonoids, despite the unfavorable reaction conditions.

Within the framework of the invention, the starting flavonoids are preferably reacted after solubilization in one of the organic solvents mentioned above, such as toluene, chloroform, pyridine or acetone, the acylating agent itself being dissolved in this organic phase.

Phase transfer agents can advantageously be used to facilitate the reaction, examples being halides or hydroxides, such as halogenosulfates, for example tetrabutylammonium halogenosulfates, or benzyltriethylammonium chloride. The reaction is carried out in the presence of a base in order to activate the hydroxyl groups. Bases are selected for example from organic bases such as pyridine, or inorganic bases such as sodium or potassium carbonate, particularly in the form of a saturated aqueous solution.

It is then easy to recover the resulting acylated derivative, constituting the flavonoid ester according to the invention, from the reaction mixture by decantation of the phases and treatment of each of the phases in order to recover the total amount of flavonoid ester formed.

Within the framework of the invention, the yields obtained are generally very good and can be of the order of 50% or more, the few exceptions being when it is desired to prepare monoacylated derivatives.

The starting flavonoids are generally commercially available products.

However, these substances can be extracted from plants in a manner known to those skilled in the art. The purified fractions are preferred and attempts have been made to extract therefrom the flavonoids with a ketone group in the 4-position.

Within the framework of the invention, it is advantageous to use the flavonoids containing at least one or several C-heteroside and O-heteroside linkages. Examples of the oses are rhamnose, galactose, glucose and arabinose, which may or may not be substituted, the heteroside preferably being selected from tiliroside, orientin, shaftoside, saponarin, rutin, hesperidin and diosmin, without implying a limitation.

The esters of the invention afford effective protection of the hydroxyl groups of the starting flavonoids, while at the same time making it possible to promote the transport of these esters through biological membranes.

Within the framework of the invention, it has been possible to discover, totally unexpectedly, that the esterases present in cell tissues, particularly in the epidermis, are capable of cleaving one or more ester groups thus formed in the flavonoid esters of the invention and of regenerating the starting flavonoids as well as the organic monoacid used.

Therefore the invention makes it possible to use the flavonoids released in this way, having their own, preserved activity (activities), in combination with the organic monoacids, which can thus act in a synergistic manner.

Insofar as this organic monoacid, for example sorbic acid or ascorbic acid, has its own activity, the invention enables the activity of this acid to be combined with the activity of the flavonoid.

The flavonoid esters according to the invention can be used as cosmetic agents.

In this context, the flavonoid esters according to the invention are generally mixed with a cosmetically acceptable excipient, vehicle or carrier. The amount of the flavonoid esters according to the invention which is effective for a cosmetic activity is generally between 0.0001% and 10% by weight, preferably between 0.01 and 5% by weight, based on the final weight of the cosmetic composition. The advantageous cosmetic activity of the flavonoid esters according to the invention is based on a free radical inhibiting activity, an antioxidizing activity, an inhibiting activity on blotchiness, an inhibiting effect on chemical, physical or actinic erythema, a treatment for sensitive skin, a draining treatment, a slimming treatment, an anti-wrinkle treatment, a stimulating effect on the synthesis of the components of the extracellular matrix, particularly elastin, a toning effect, an improving effect on the elasticity of the skin or the epidermis, and an anti-ageing effect.

By virtue of the liposoluble property of the flavonoid esters according to the invention, these flavonoid esters can easily be incorporated into conventional cosmetic formulations, especially those in the form of creams, ointments, emulsions, gels or lotions. The flavonoid esters can be used in the free state or in the encapsulated state, particularly by being at least partially incorporated in liposomes.

According to the invention, the above-mentioned flavonoid esters can also be used in dietetics or in agri-foodstuff compositions.

The flavonoid esters according to the invention make it possible to improve the stability of foodstuffs by virtue of their free radical inhibiting and antioxidizing activity. Agri-foodstuff compositions which may be mentioned are drinks, fruit juices, tonic drinks and dairy products.

The invention also makes it possible to prepare pharmaceutical compositions.

In this context, the dosage used is that which is normally recommended for flavonoids when considering their known activities.

In the context of application to the epidermis, it will be preferable to use topical pharmaceutical compositions in which the flavonoid esters according to the invention will be mixed with a pharmaceutically acceptable excipient compatible with the epidermis. These pharmaceutical compositions can thus be formulated to have a tonic effect on the veins, for example in the form of an ointment, to increase the strength of the blood capillaries, to obtain an inhibiting effect on blotchiness or to have an inhibiting effect on chemical, physical or actinic erythema.

The invention further relates to a method of cosmetic or pharmaceutical treatment which comprises applying, to any mammal and preferably a human being in need thereof, a cosmetically or therapeutically effective amount of at least one flavonoid ester mentioned above, particularly by the topical route.

In one advantageous embodiment, a cosmetic treatment is carried out.

In another advantageous embodiment of the invention, a therapeutic treatment is carried out.

Other objects, characteristics and advantages of the invention will become clearly apparent from the following Examples, which are given by way of illustration and cannot therefore in any way limit the scope of the invention.

In the Examples, all the percentages are given by weight, unless indicated otherwise, the temperature is given in ° C. or is room temperature and the pressure is atmospheric pressure, unless indicated otherwise.

The most widely tested products are hesperitin, quercetin and hesperidin, rendered lipophilic by palmitic acid (C16), lauric acid (C12) and butyric acid (C4).

EXAMPLE 1
Quercetin (Flavonol Family) Pentaacylated by C12

5 g of flavonoid (16.55 mmol) are placed in a dry 1 l round-bottomed flask and 200 ml of toluene are added. Lauroyl chloride (165.5 mmol) and then saturated $K_2CO_3$ solution are added. The solution is refluxed for 1 h. The toluene phase is separated off and the aqueous phase is extracted with chloroform. Both the toluene and chloroform phases are washed with saturated aqueous NaCl solution and then dried over sodium sulfate and concentrated. The crude product obtained (13 g) is purified on silica gel (700 g) using chloroform/hexane (50/50) and then chloroform as the eluents. The product fractions are combined, concentrated and dried on a vacuum pump for 24 h to give 10.83 g of quercetin pentaacylated by C12 (yellow powder). Yield: 54%.

EXAMPLE 2
Quercetin Pentaacylated by C12

165.5 mmol of lauroyl chloride are added to 5 g of quercetin (16.55 mmol) in 100 ml of pyridine. The mixture is heated at 100° C. for 6 hours. The solution is concentrated under vacuum and the crude product is dissolved in 200 ml of dichloromethane. After washing with aqueous solutions of $CuSO_4$ and then NaCl, the solution is dried over $Na_2SO_4$ and then concentrated. The crude product (16 g) is purified on a column of silica (800 g) using dichloromethane/hexane (2/3) as the eluent to give 12.23 g of quercetin pentaacylated by C12. Yield: 61%.

EXAMPLE 3
Quercetin Pentaacylated by C16

5 g of flavonoid (16.55 mmol) are placed in a dry 1 l round-bottomed flask and 200 ml of toluene are added. Palmitoyl chloride (165.5 mmol) and then saturated $K_2CO_3$ solution (100 ml) are added. The solution is refluxed for 1 h. The toluene phase is separated off and the aqueous phase is extracted with chloroform. Both the toluene and chloroform phases are washed with saturated aqueous NaCl solution and then dried over sodium sulfate and concentrated. The crude product obtained (19.3 g) is purified on silica gel (500 g) using chloroform/hexane (50/50) and then chloroform as the eluents. The product fractions are combined, concentrated and dried on a vacuum pump for 24 h to give 12.84 g of quercetin pentaacylated by C16 (white powder). Yield: 52%.

EXAMPLE 4
Quercetin Pentaacylated by C16

165.5 mmol of palmitoyl chloride are added to 5 g of quercetin (16.55 mmol) in 100 ml of pyridine. The mixture is heated at 100° C. for 6 hours. The solution is concentrated under vacuum and the crude product is dissolved in 200 ml of dichloromethane. After washing with solutions of $CuSO_4$ and then NaCl, the solution is dried over $Na_2SO_4$ and then concentrated. The crude product (17.6 g) is purified on a column of silica (800 g) using dichloromethane/hexane (1/3) as the eluent to give 14.3 g of quercetin pentaacylated by C16. Yield: 58%.

EXAMPLE 5
Quercetin Pentaacylated by C4

The protocol of Example 2 is followed with 5 g of quercetin and 165.5 mmol of butyric anhydride; the crude product (8.34 g) is purified on a column of silica (700 g) using $CHCl_3$/hexane (2/3) as the eluent to give 5.18 g of quercetin pentaacylated by C4. Yield: 48%.

EXAMPLE 6
Hesperitin (Flavanone Family) Diacylated by C12

5 g of flavonoid (16.55 mmol) are placed in a dry 1 l round-bottomed flask and 200 ml of toluene are added. Lauroyl chloride (26.5 mmol) and then saturated aqueous $K_2CO_3$ solution (100 ml) are added. The solution is refluxed for 1 h. The toluene phase is separated off and the aqueous phase is extracted with chloroform. Both the toluene and chloroform phases are washed with saturated aqueous NaCl solution and then dried over sodium sulfate and concentrated. The crude product obtained (10.8 g) is purified on silica gel (500 g) using dichloromethane/hexane (1/4) and then chloroform as the eluents. The product fractions are combined, concentrated and dried on a vacuum pump for 24 h to give 7.1 g of hesperitin diacylated by C12 (oil). Yield: 64%.

EXAMPLE 7
Hesperitin Monoacylated by C12

5 g of flavonoid (16.55 mmol) and 70 ml of chloroform are placed in a dry 1 l round-bottomed flask. Lauroyl chloride (3.85 ml, 16.55 mmol) and then pyridine (1.88 ml, 16.55 mmol) are added and the reaction mixture is then refluxed for 15 h. After dilution with 150 ml of chloroform, the organic phase is separated off, washed with aqueous NaCl solution, dried over $Na_2SO_4$ and concentrated to give 11.28 g of a red oil. Purification of the crude product on a column of silica (400 g) using dichloromethane as the eluent gives 1.98 g of hesperitin diacylated by C12 (yield: 18%) and 0.81 g of hesperitin monoacylated by C12 (yield: 10%).

EXAMPLE 8
Hesperitin Monoacylated by C12

5 g of flavonoid (16.55 mmol) and 100 ml of pyridine are placed in a dry 1 l round-bottomed flask, followed by 16.55 mmol of lauroyl chloride. The solution is stirred at ordinary temperature for 1 hour and evaporated to dryness. The crude product is dissolved in 200 ml of chloroform, washed with $CuSO_4$ solution and then with aqueous NaCl solution, dried over $Na_2SO_4$ and concentrated to give 8.92 g of a crude product, which is chromatographed on a column of silica (400 g) using dichloromethane as the eluent to give 2.74 g of hesperitin diacylated by C12 (yield: 25%) and 0.96 g of hesperitin monoacylated by C12 (yield: 12%). These products can be used in the form of the crude product, in the form of the product purified in the mixture or in the form of products purified independently.

EXAMPLE 9
Hesperitin Monoacylated and Diacylated by C12

The protocol of Example 2 is followed with 5 g of hesperitin and 16.55 mmol of lauroyl chloride; the crude product (8.92 g) is not purified; it contains hesperitin monoacylated and diacylated by C12 (yield: 37%) and is used as such.

EXAMPLE 10
Hesperitin Monoacylated and Diacylated by C16

The protocol of Example 2 is followed with 5 g of hesperitin and 16.55 mmol of palmitoyl chloride; the crude product (10.3 g) is purified on a column of silica (600 g) using $CH_2Cl_2$/hexane (1/1) and $CH_2Cl_2$ as the eluents to give 2.7 g of hesperitin diacylated by C16 (yield: 21%) and 0.89 g of hesperitin monoacylated by C16 (yield: 10%), which can be used in the form of the crude product, in the form of the product purified in the mixture or in the form of products purified independently.

EXAMPLE 11
Hesperitin Triacylated by C16

The protocol of Example 2 is followed with 5 g of hesperitin and 99.3 mmol of palmitoyl chloride; the crude product is purified on a column of silica (500 g) using $CH_2Cl_2$/hexane (1/1) as the eluent to give 10 g of hesperitin triacylated by C16. Yield: 59.4%.

EXAMPLE 12
Hesperitin Triacylated by C4

The protocol of Example 2 is followed with 5 g of hesperitin and 99.3 mmol of butyric anhydride; the crude product (13 g) is purified on a column of silica (700 g) using $CHCl_3$/hexane (2/3) as the eluent to give 4.61 g of hesperitin triacylated by C4. Yield: 55%.

EXAMPLE 13
Hesperitin Triacylated by C18:0

The protocol of Example 2 is followed with 5 g of hesperitin and 99.3 mmol of stearoyl chloride; the crude product can be used as such or purified on a column of silica to give hesperitin triacylated by C18:0.

EXAMPLE 14
Hesperitin Triacylated by C18:1

The protocol of Example 2 is followed with 5 g of hesperitin and 99.3 mmol of oleoyl chloride; the crude product can be used as such or purified on a column of silica to give hesperitin triacylated by C18:1.

EXAMPLE 15
Hesperitin Triacylated by C18:2

The protocol of Example 2 is followed with 5 g of hesperitin and 99.3 mmol of linoleoyl chloride; the crude product can be used as such or purified on a column of silica to give hesperitin triacylated by C18:2.

EXAMPLE 16
Hesperitin Triacylated by C18:3

The protocol of Example 2 is followed with 5 g of hesperitin and 99.3 mmol of linolenoyl chloride; the crude product can be used as such or purified on a column of silica to give hesperitin triacylated by C18:3.

EXAMPLE 17
Hesperitin Triacylated by C11:1

The protocol of Example 2 is followed with 5 g of hesperitin and 99.3 mmol of undecylenoyl chloride; the crude product can be used as such or purified on a column of silica to give hesperitin triacylated by C11:1.

EXAMPLE 18
Hesperitin Triacylated by C7

The protocol of Example 2 is followed with 5 g of hesperitin and 99.3 mmol of heptanoyl chloride; the crude product can be used as such or purified on a column of silica to give hesperitin triacylated by C7.

EXAMPLE 19
Hesperitin Triacylated by Succinic Acid

The protocol of Example 2 is followed with 5 g of hesperitin and 99.3 mmol of succinic anhydride; the crude product can be used as such or purified on a column of silica to give hesperitin triacylated by succinic acid.

EXAMPLE 20
Acylated Ester of Apigenin of the Flavone Family

In this Example the procedure is as described in Example 6 except that the hesperitin is replaced with apigenin.

Triacylated apigenin is obtained. It should be noted that apigenin is a compound of formula (II) containing 3 OH groups.

Manufacturing variants can be carried out by using different reaction conditions or by changing the nature of the acid used, as in Examples 7 to 19.

EXAMPLE 21
Acylated Ester of Naringenin of the Flavanone Family, Like Hesperitin An acylated ester of naringenin can be prepared by using the reaction conditions of any one of Examples 6 to 19 except that the hesperitin is replaced with naringenin. A triacylated derivative is obtained.

EXAMPLE 22
Hesperidin (Glycosylated Flavanone Family) Octaacylated by C12

The protocol of Example 2 is followed with 5 g of hesperidin and 131.02 mmol of lauroyl chloride; the crude product (15 g) can be purified on a column of silica to give hesperidin octaacylated by C12.

EXAMPLE 23
Palmitic Acid Ester of Hesperidin of the Glycosylated Flavanone Family The title palmitate ester of this Example is obtained by following the procedure described in Example 22 except that the lauroyl chloride is replaced with palmitoyl chloride.

EXAMPLE 24
Flavonoid Ester of Naringin of the Glycosylated Flavanone Family, Like Hesperidin An acylated ester of naringin is prepared by using the reaction conditions of Example 22 except that the hesperidin is replaced with naringin.

EXAMPLE 25
Acylated Ester of Diosmin of the Glycosylated Flavone Family

An acylated ester of diosmin, for example diosmin acylated with lauric acid, can be prepared by using the reaction conditions of Example 6 and replacing the hesperitin with diosmin.

EXAMPLE 26
Acylated Ester of Rutin of the Glycosylated Flavonol Family

A lauric acid ester of rutin can be prepared by using the reaction conditions of Example 6.

In the case of Examples 23 to 26 it is also possible to change the esterifying acid or the reaction conditions, as in the variants forming the subject of Examples 7 to 19.

EXAMPLE 27

Oxidation Stability Test on Flavonoids in Simple Preparations

A solution of hesperitin containing 31.1 g/l (i.e. 0.103 M) is prepared in ethoxy-diglycol. The pH is adjusted to 5 or 6 and then 10 g/l of a preservative based on parabens are added to the mixture in order to avoid bacterial pollution. In a separate procedure, the product of the invention resulting from Example 9 is also made up into a 0.103 M solution in ethoxydiglycol, the pH is adjusted to 5 or 6 and then 10 g/l of a preservative based on parabens are again added to the mixture. At identical molar concentrations, the two products are therefore compared for their oxidation stability, the color parameters being used as the stability indicators. The color references given in the Examples which follow refer to the Pantone colors as used in all the paint color charts well known to those skilled in the art.

TABLE I

Color of the solutions 1 day after manufacture:

| | Hesperitin | | | Acylated hesperitin according to Example 9 of the invention | | |
|---|---|---|---|---|---|---|
| | 20° C. | 4° C. | 45° C. | 20° C. | 4° C. | 45° C. |
| pH 5 | 157C orange to brown | 157C orange to brown | 157C orange to brown | 1205C very light yellow | 120C | 120C |
| pH 6 | 157C orange to brown | 157C orange to brown | 157C orange to brown | 1215C light yellow | 120C | 113C |

TABLE II

Color of the solutions 21 days after manufacture:

| | Hesperitin | | | Acylated hesperitin according to Example 9 of the invention | | |
|---|---|---|---|---|---|---|
| | 20° C. | 4° C. | 45° C. | 20° C. | 4° C. | 45° C. |
| pH 5 | black + precipitate | black + precipitate | black + precipitate | 1205C very light yellow | 1205C | 120C |
| pH 6 | black+ precipitate | black+ precipitate | black+ precipitate | 1215C light yellow | 1205C | 121C |

Here, rendering the flavonoids lipophilic by acylation can therefore be a means of stabilizing these substances towards oxidation.

EXAMPLE 28

Oxidation Stability Test on Flavonoids in Complex Preparations (Emulsions)

Composition of the formulation:

| Phase | INCI name | g/100 g |
|---|---|---|
| A | water | qsp 100 |
| B | PEG2 stearate SE, ceteareth 25, hydrogenated coconut oil, mineral oil | 16.0 |
| C | water | 3.0 |
| | polyacrylamide, isoparaffin, laureth-7 | 1.0 |
| D | phenoxyethanol, methylparaben, ethylparaben, propylparaben, butylparaben butylene glycol | 1.0 1.0 |
| E | ethoxydiglycol with or without free flavonoid, with or without product of the invention | 0.01–40 |

TABLE III

Stability test:

| Cream | Control | Hesperitin 520 µM | Product of the invention according to Example 9 520 µM | Hesperitin 1043 µM | Product of the invention according to Example 9 1043 µM |
|---|---|---|---|---|---|
| pH | 6.94 | 6.76 | 6.97 | 6.9 | 6.9 |
| T 1 day | white | light beige | white | more pronounced beige | white |
| T 7 days | white | yellow +++ | very slight yellow glints | very yellow +++++ | yellow glints |
| T 25 days | white | yellow +++ | very slight yellow glints | very yellow +++++ | yellow glints |
| T 35 days | white | yellow +++ | very slight yellow glints | very yellow ++++++ | yellow glints |

After studying the stabilities over about 1 month, it can be said that the color of the formulations containing flavonoids used in the form which has not been rendered lipophilic undergoes an extremely unfavorable change at 45° C.

The formulation whose color stability is the closest to that of the control is the one containing 520 µmol/l of flavonoid which has been rendered lipophilic.

At constant molarities, the creams containing flavonoids which have been rendered lipophilic are more stable than those containing flavonoids, a phenomenon which is accentuated when the flavonoid is introduced in excess into the cream. Rendering the flavonoids lipophilic therefore stabilizes the color in emulsions.

EXAMPLE 29

Determination of the Anti-Elastase Activity

The enzymatic substrate elastin-rhodamine is dissolved in TrisHCl buffer (31.52 g of TrisHCl, water qsp 1000 ml) of pH 8.8 at a rate of 15 mg/ml. 1 mg of human leukocytic elastase is dissolved in 20 ml of TrisHCl buffer. The products of the invention are evaluated for their capacity to inhibit the degradation of elastin, which can be followed by fluorescence (excitation at 530 nm; emission at 590 nm) after the incubation, for 20 min at 37° C., of a mixture comprising the substrate, the enzyme and the inhibitor to be tested. The results are given as % inhibition relative to the inhibitor-free control.

The products of the invention of Example 7 and Example 9, and the unmodified flavonoid, are solubilized in ethoxydiglycol:

TABLE IV

Anti-elastase test:

| Test concentration (mol/l) | Hesperitin | Product of the invention (Ex. 7) | Product of the invention (Ex. 9) |
|---|---|---|---|
| 0.103 | 100 | 100 | 100 |
| $1.03^{-3}$ | 20 | 50 | 44 |
| $1.03^{-4}$ | 24 | 36 | 38 |
| $1.03^{-5}$ | 0 | 34 | 34 |

The products of the invention of Example 6, and the unmodified flavonoid, are solubilized in ethoxydiglycol:

TABLE V

Anti-elastase test:

| Test concentration (mol/l) | Hesperitin | Product of the invention (Ex. 6) |
|---|---|---|
| 0.103 | 100 | 100 |
| $1.03^{-3}$ | 20 | 65 |
| $1.03^{-5}$ | 0 | 29 |

The anti-elastase activity is stronger for the flavonoids which have been rendered lipophilic than for the flavonoids before they have been rendered lipophilic.

EXAMPLE 30
Determination of the Free Radical Inhibiting Activity in Vitro

A 60 μM solution of 1,1-diphenyl-2-picrylhydrazyl in ethanol is placed in contact, for 30 minutes at room temperature, with a sample originating from the products of the invention whose free radical inhibiting power is to be determined. The drop in absorbance is then measured at 520 nm and the results are given as the percentage decrease in OD caused by the test compound relative to the solvent used. The higher the percentage decrease, the stronger will be the free radical inhibiting activity of the active ingredient tested.

The products of the invention are dissolved in DMSO; the results (DMSO control subtracted) are given as % free radical inhibiting activity as described above:

TABLE VI

| Compound at 25 mM | Free radical inhibiting activity |
|---|---|
| Hesperitin | 42% |
| Product of Example 6 | 67% |

The products of the invention are dissolved in ethoxydiglycol; the results (ethoxy-diglycol control subtracted) are given as % free radical inhibiting activity as described above:

TABLE VII

| Concentration in mol/l | Hesperitin | Product of the invention according to Example 8 | Product of the invention according to Example 9 |
|---|---|---|---|
| 0.103 | 94 | 93 | 95 |
| $1.03^{-3}$ | 28 | 10 | 17 |
| $1.03^{-5}$ | 8 | 6 | 12 |

The free radical inhibiting activity is preserved after the flavonoids have been rendered lipophilic, which is totally unexpected for those skilled in the art.

EXAMPLE 31
Use of the Products of the Invention in Cosmetic or Pharmaceutical Formulations of the Oil-in-water Emulsion Type Formulation 31a

| A | Water | qsp | 100 |
|---|---|---|---|
|   | Butylene glycol | 2 | |
|   | Glycerol | 3 | |
|   | Sodium dihydroxycetyl phosphate, isopropyl hydroxycetyl ether | 2 | |
|   | Butylene glycol, methylparaben, ethylparaben, propylparaben | 2 | |
|   | Products of the invention | 0.0001–5% | |
| B | Glycol stearate SE | 14 | |
|   | Triisononanoin | 5 | |
|   | Octyl cocoate | 6 | |

Formulation 31b

| Water | qsp | 100 |
|---|---|---|
| Butylene glycol | 2 | |
| Glycerol | 3 | |
| Polyacrylamide, isoparaffin, laureth-7 | 2.8 | |
| Butylene glycol, methylparaben, ethylparaben, propylparaben | 2 | |
| Phenoxyethanol, methylparaben, propylparaben, butylparaben, ethylparaben | 2 | |
| Butylene glycol | 0.5 | |
| Products of the invention | 0.0001–5% | |

Formulation 31c

| A | Carbomer | 0.50 | |
|---|---|---|---|
|   | Propylene glycol | 3 | |
|   | Glycerol | 5 | |
|   | Water | qsp | 100 |
| B | Octyl cocoate | 5 | |
|   | Bisabolol | 0.30 | |
|   | Dimethicone | 0.30 | |
| C | Sodium hydroxide | 1.60 | |
| D | Phenoxyethanol, methylparaben, propylparaben, butylparaben, ethylparaben | 0.50 | |
| E | Perfume | 0.3 | |
| F | Products of the invention | 0.0001–5% | |

EXAMPLE 32
Use of the Products of the Invention in a Formulation of the Water-in-oil Type

| A. | PEG 30 dipolyhydroxystearate | 3 | |
|---|---|---|---|
|   | Capric triglycerides | 3 | |
|   | Cetearyl octanoate | 4 | |
|   | Dibutyl adipate | 3 | |
|   | Grape seed oil | 1.5 | |
|   | Jojoba oil | 1.5 | |
|   | Phenoxyethanol, methylparaben, propylparaben, butylparaben, ethylparaben | 0.5 | |
| B | Glycerol | 3 | |
|   | Butylene glycol | 3 | |
|   | Magnesium sulfate | 0.5 | |
|   | EDTA | 0.05 | |
|   | Water | qsp | 100 |
| C | Cyclomethicone | 1 | |
|   | Dimethicone | 1 | |

-continued

| | | |
|---|---|---|
| D | Perfume | 0.3 |
| E | Product of the invention | 0.0001–5% |

EXAMPLE 33
Use of the Products of the Invention in a Formulation of the Shampoo or Shower Gel Type

| | | |
|---|---|---|
| A | Xanthan gum | 0.8 |
| | Water | qsp 100 |
| B | Butylene glycol, methylparaben, ethylparaben, propylparaben | 0.5 |
| | Phenoxyethanol, methylparaben, propylparaben, butylparaben, ethylparaben | 0.5 |
| C | Citric acid | 0.8 |
| D | Sodium laureth sulfate | 40.0 |
| E | Product of the invention | 0.0001–1% |

EXAMPLE 34
Use of the Products of the Invention in a Formulation of the Lipstick or Other Anhydrous Product Type

| | | |
|---|---|---|
| A | Mineral wax | 17.0 |
| | Isostearyl isostearate | 31.5 |
| | Propylene glycol dipelargonate | 2.6 |
| | Propylene glycol isostearate | 1.7 |
| | PEG 8 beeswax | 3.0 |
| | Hydrogenated palm kernel oil, glycerides, hydrogenated palm glyceride | 3.4 |
| | Lanolin oil | 3.4 |
| | Sesame oil | 1.7 |
| | Tribehenin | 1.7 |
| | Cetyl lactate | 1.7 |
| | Mineral oil, lanolin alcohol | 3.0 |
| B | Castor oil | qsp 100 |
| | Titanium dioxide | 3.9 |
| | CI 15850:1 | 0.616 |
| | CI 45410:1 | 0.256 |
| | CI 19140:1 | 0.048 |
| | CI 77491 | 2.048 |
| C | Product of the invention | 0.0001–5 |

EXAMPLE 35
Use of the Products of the Invention in an Aqueous Gel Formulation (Eye Contour Gels, Slimming Gels, etc.)

| | |
|---|---|
| Water | qsp 100 |
| Carbomer | 0.5 |
| Butylene glycol | 15 |
| Phenoxyethanol, methylparaben, propylparaben, butylparaben, ethylparaben | 0.5 |
| Product of the invention | 0.0001–5 |

EXAMPLE 36
Toxicological Studies Carried Out on the Product of the Invention of Example 9

The product of Example 9 (6 g) is dissolved in ethoxydiglycol (93 g), and 1 g of a mixture containing different parabens, used as bacterial preservatives, is added to the mixture. This preparation is used for the following toxicity studies:

a) Oral Toxicity

The tests were performed by the protocol in accordance with the OECD guideline relating to the study of acute oral toxicity (no. 401 of Feb. 24, 1987), at maximum doses of 5 g/kg body weight, and did not cause any macroscopic lesions attributable to a toxic effect of the product.

The above preparation, manufactured from the products of the invention and used orally at a dose below 5 g/kg, therefore has zero toxicity.

b) Eye Irritation

The tests were performed by the official method in accordance with the decree of May 3, 1990 (Official Journal of the French Republic of Nov. 14, 1990) with the above-described preparation and did not cause any lesions of the iris or cornea. The above preparation, manufactured from the products of the invention and instilled pure, appeared to be non-irritant and the eye tolerance can be considered to be very good.

c) Skin Irritation

The tests were performed by the official method in accordance with the decree of Feb. 1, 1982 (Official Journal of the French Republic of Feb. 21, 1982) with the products of the invention (Examples 12 and 15) and did not cause any irritation phenomena.

The above preparation, manufactured from the products of the invention and instilled pure, appeared to be non-irritant and the skin tolerance can be considered to be excellent.

d) Testing for the Sensitizing Power

Maximization tests were performed by a protocol adapted from the method described by Magnusson and Kligman (J. INVEST. DERM. 1969, 52, 268–276). The above preparation, manufactured from the products of the invention and instilled pure, did not cause any macroscopic reactions indicative of a sensitization reaction. The products of the invention can therefore be considered to be hypoallergenic (class I).

What is claimed is:

1. A method of providing cosmetic care comprising a topical application, to zones of the skin of a person in need thereof, of a cosmetically effective amount of hesperitin comprising at least one lauroyl substituent, optionally in a cosmetically acceptable excipient.

2. A method of providing cosmetic care with anti-elastase activity comprising a topical application, to zones of the skin of a person in need thereof, of a cosmetically anti-elastase effective amount of hesperitin comprising at least one lauroyl substituent, optionally in a cosmetically acceptable excipient.

3. A method of providing cosmetic care with free radical inhibiting activity comprising a topical application, to zones of the skin of a person in need thereof, of a cosmetically free radical-inhibiting effective amount of hesperitin comprising at least one lauroyl substituent, optionally in a cosmetically acceptable excipient.

4. The method of claim 1, wherein said hesperitin comprising at least one lauroyl substituent is selected from the group consisting of monolauroyl substituted hesperitin, dilauroyl substituted hesperitin and mixtures thereof.

5. The method of claim 2, wherein said hesperitin comprising at least one lauroyl substituent is selected from the group consisting of monolauroyl substituted hesperitin, dilauroyl substituted hesperitin and mixtures thereof.

6. The method of claim 3, wherein said hesperitin comprising at least one lauroyl substituent is selected from the group consisting of monolauroyl substituted hesperitin, dilauroyl substituted hesperitin and mixtures thereof.

7. The method of claim 1, wherein said lauroyl substituted hesperitin is present in a cosmetic composition at a concentration ranging between 0.0001% and 10% by weight based on the final total weight of the composition.

8. The method of claim 1, wherein said lauroyl substituted hesperitin is present in a cosmetic composition at a concentration ranging between 0.01% and 5% by weight based on the final total weight of the composition.

9. The method of claim 2, wherein said lauroyl substituted hesperitin is present in a cosmetic composition at a concentration ranging between 0.0001% and 10% by weight based on the final total weight of the composition.

10. The method of claim 2, wherein said lauroyl substituted hesperitin is present in a cosmetic composition at a concentration ranging between 0.01% and 5% by weight based on the final total weight of the composition.

11. The method of claim 3, wherein said lauroyl substituted hesperitin is present in a cosmetic composition at a concentration ranging between 0.0001% and 10% by weight based on the final total weight of the composition.

12. The method of claim 3, wherein said lauroyl substituted hesperitin is present in a cosmetic composition at a concentration ranging between 0.01% and 5% by weight based on the final total weight of the composition.

* * * * *